United States Patent
Alani et al.

(10) Patent No.: US 8,501,219 B2
(45) Date of Patent: *Aug. 6, 2013

(54) FLAVORING SYSTEMS FOR PHARMACEUTICAL COMPOSITIONS AND METHODS OF MAKING SUCH COMPOSITIONS

(75) Inventors: Laman Alani, Hillsborough, CA (US); Donald P. Gauwitz, McHenry, IL (US); Dilip Kaul, Hillsborough, NJ (US); John M. Lipari, Racine, WI (US); Soumojeet Ghosh, Gurnee, IL (US); Kennan C. Marsh, Lake Forest, IL (US); Richard H. Whelan, Norfolk, MA (US); Vanik D. Petrossian, Waban, MA (US)

(73) Assignee: AbbVie Inc., North Chicago, IL (US)

( * ) Notice: Subject to any disclaimer, the term of this patent is extended or adjusted under 35 U.S.C. 154(b) by 509 days.

This patent is subject to a terminal disclaimer.

(21) Appl. No.: 12/687,479

(22) Filed: Jan. 14, 2010

(65) Prior Publication Data

US 2010/0280055 A1 Nov. 4, 2010

Related U.S. Application Data

(63) Continuation of application No. 11/118,733, filed on Apr. 29, 2005, now abandoned, which is a continuation of application No. 09/946,085, filed on Sep. 4, 2001, now Pat. No. 6,911,214.

(60) Provisional application No. 60/230,095, filed on Sep. 5, 2000.

(51) Int. Cl.
A61K 47/00 (2006.01)
A61K 9/00 (2006.01)

(52) U.S. Cl.
USPC .......................................... 424/439; 424/400

(58) Field of Classification Search
USPC ................................................ 424/400, 439
See application file for complete search history.

(56) References Cited

U.S. PATENT DOCUMENTS

| | | | |
|---|---|---|---|
| 4,484,401 A | 11/1984 | Pitts | |
| 5,484,801 A * | 1/1996 | Al-Razzak et al. | 514/365 |
| 5,541,206 A | 7/1996 | Kempf et al. | |
| 5,559,158 A | 9/1996 | Al-Razzak et al. | |
| 5,616,621 A * | 4/1997 | Popli et al. | 514/772.4 |
| 5,648,497 A | 7/1997 | Kempf et al. | |
| 5,905,068 A | 5/1999 | Chen et al. | |
| 5,914,332 A | 6/1999 | Sham et al. | |
| 5,948,436 A | 9/1999 | Al-Razzak et al. | |
| 6,440,946 B1 * | 8/2002 | Kiso et al. | 514/45 |
| 6,911,214 B2 * | 6/2005 | Alani et al. | 424/439 |
| 2005/0191324 A1 | 9/2005 | Alani et al. | |

FOREIGN PATENT DOCUMENTS

| | | |
|---|---|---|
| WO | WO9520384 A1 | 8/1995 |
| WO | WO9746222 A1 | 12/1997 |
| WO | WO9822106 A1 | 5/1998 |

OTHER PUBLICATIONS

Abbott Laboratories: "Norvir" Product Labeling, Norvir, Online, Mar. 2001.
International Search Report for Application No. PCT/US01/27415, mailed on Mar. 8, 2002, 4 pages.
Ohta, Yukari et al., "New Drugs—Reports of new drugs recently approved by the FDA: Ritonavir. XP001061208.," Bioorganic & Medicinal Chemistry, vol. 5 (3), pp. 461-462, 1997.
Written Opinion for Application No. PCT/US01/27415, mailed on Jul. 18, 2003, 4 pages.
Office Action for U.S. Appl. No. 09/655,192, mailed on Oct. 24, 2001, 8 pages.
Office Action for U.S. Appl. No. 11/118,733, mailed on Jul. 14, 2009, 9 pages.
Office Action for U.S. Appl. No. 09/946,085, mailed on Aug. 11, 2004, 5 pages.
Office Action for U.S. Appl. No. 09/946,085, mailed on Apr. 9, 2003, 6 pages.

* cited by examiner

Primary Examiner — Blessing Fubara
(74) Attorney, Agent, or Firm — Bradley E. Davis

(57) ABSTRACT

A flavoring system for a liquid pharmaceutical composition and pharmaceutical compositions containing such flavoring systems are disclosed. Flavoring systems of the invention include at least one sweetening agent, at least two flavored ingredients, and at least one flavor modifier selected from the group consisting of citric acid, sodium citrate, sodium chloride, and mixtures thereof. At least two of the flavored ingredients are selected from the group consisting of a vanilla flavored ingredient, a peppermint flavored ingredient, a menthol flavored ingredient, a cotton candy flavored ingredient, and mixtures thereof. The one or more sweetening agents comprise glycerin, monoammonium glycyrrhizinate, saccharin sodium, acesulfame potassium, high fructose corn syrup, and/or mixtures thereof. Pharmaceutical compositions of the invention include a flavoring system of the invention, a solvent system, and at least one pharmaceutically active agent, such as lopinavir or derivatives thereof, ritonavir or derivatives thereof, or mixtures thereof. Methods for making such liquid pharmaceutical compositions are also disclosed.

29 Claims, No Drawings

FLAVORING SYSTEMS FOR PHARMACEUTICAL COMPOSITIONS AND METHODS OF MAKING SUCH COMPOSITIONS

This application is a continuation of and claims priority to U.S. patent application Ser. No. 11/118,733 filed on Apr. 29, 2005, which is a continuation of and claims priority to U.S. patent application Ser. No. 09/946,085 filed Sep. 4, 2001 and issued as U.S. Pat. No. 6,911,214 on Jun. 28, 2005, which claims priority to U.S. Provisional Patent Application No. 60/230,095 filed Sep. 5, 2000. The entire contents of these patent applications are incorporated by reference into this patent application.

FIELD OF THE INVENTION

This invention relates to flavoring systems for pharmaceutical compositions, pharmaceutical compositions containing such flavoring systems, and methods of making such compositions. In particular, this invention is related to flavoring systems for liquid pharmaceutical compositions containing ritonavir or derivatives thereof, lopinavir or derivatives thereof, and mixtures of any of the above. The invention is also directed toward pharmaceutical compositions containing the flavoring systems of the invention and toward methods of making these pharmaceutical compositions.

BACKGROUND OF THE INVENTION

The pharmaceutically active agents lopinavir and ritonavir are well known inhibitors of the Human Immunodeficiency Virus (HIV), which is the causative organism of Acquired Immunodeficiency Syndrome (AIDS). Both ritonavir and lopinavir inhibit HIV by inhibiting HIV proteases. Proteases are enzymes that cleave proteins at specific peptide bonds, and many significant biological functions are controlled or mediated by proteases and their inhibitors. By administering pharmaceutically active agents that inhibit HIV proteases, the replication of HIV in humans can be controlled or ceased.

Although much progress has been made toward treating AIDS, none of the current treatments have proven to be totally effective in reversing the disease. In addition, many of the pharmaceutically active agents useful in treating AIDS have a bitter taste that discourages patients from complying with their drug taking regimen. Therefore, improving the taste of liquid compositions containing pharmaceutically active agents, such as lopinavir and ritonavir, is important in the fight against AIDS.

Flavoring agents for liquid pharmaceuticals are well known. For example, U.S. Pat. No. 5,484,801, which issued on Jan. 16, 1996, discloses the use of such flavoring agents as wild cherry flavor, banana flavor, strawberry flavor, sodium saccharin, citric acid, chocolate mint, and other flavor enhancers in pharmaceutical compositions containing ritonavir. However, there remains a need for improved flavoring systems for liquid pharmaceutical compositions containing pharmaceutically active agents, such as ritonavir and/or lopinavir, which are practically insoluble in water and tend to have a bitter taste.

SUMMARY OF THE INVENTION

In general, Applicants have discovered that by increasing the number and type of ingredients in flavoring systems for liquid pharmaceutical compositions containing pharmaceutically active agents, such as lopinavir and ritonavir, the taste of pharmaceutical compositions containing these agents is improved. Flavoring systems of the invention generally contain two or more flavored ingredients, one or more sweetening agents, and one or more flavor modifiers selected from the group consisting of sodium citrate, sodium chloride, citric acid and mixtures thereof. Preferably two or more and most preferably all of the ingredients identified in the previous sentence are included as flavor modifiers in flavoring systems of the invention. The total amount of flavor modifiers included in flavoring systems of the invention is at least about 0.10% by weight and not greater than about 1.0% by weight based upon the total pharmaceutical composition containing such flavoring system. Most preferably, all of these flavor modifiers are included in the flavoring system in the following amounts by weight: sodium citrate in an amount of about 0.20%, sodium chloride in an amount of about 0.35%, and citric acid in an amount of about 0.11% based upon the total weight of the pharmaceutical composition. Unless otherwise stated herein, all weights are based upon the total weight of the pharmaceutical composition.

Flavoring systems of the invention also include at least two flavored ingredients having a vanilla, menthol, cotton candy, and/or peppermint flavor. More preferred flavoring systems of the invention include at least three of these flavored ingredients, and most preferred flavoring systems of the invention include all four of these flavored ingredients. The most preferred menthol flavored ingredient is menthol crystals, and the most preferred peppermint flavored ingredient is peppermint oil. The total amount by weight of flavored ingredients in pharmaceutical compositions containing flavoring systems of the invention is at least about 1.4% by weight and not greater than about 3.5% by weight. More preferably, the total amount of flavored ingredients in pharmaceutical compositions containing flavoring systems of the invention is at least about 2.4% by weight and not greater than about 2.8% by weight. Most preferably the total amount of flavored ingredients in pharmaceutical compositions containing flavoring systems of the invention is about 2.6% by weight. In preferred embodiments, the following flavored ingredients are included in compositions of the invention in the following amounts by weight: a cotton candy flavored ingredient in an amount of at least about 0.55% and not greater than about 1.10%; a peppermint flavored ingredient in an amount of at least about 0.15% and not greater than about 0.60%; a menthol flavored ingredient in an amount of at least about 0.03% and not greater than about 0.25%; and a vanilla flavored ingredient in an amount of at least about 0.70% and not greater than about 1.5%. In most preferred embodiments of pharmaceutical compositions of the invention, the following flavored ingredients are included in such compositions in the following amounts by weight: cotton candy flavor in an amount of about 1.00%; peppermint oil in an amount of about 0.30%; vanilla flavor in an amount of about 1.25%; and menthol crystals in an amount of about 0.05%.

At least one sweetening agent and preferably at least two sweetening agents are included in flavoring systems of the invention. More preferably, at least three sweetening agents, and most preferably at least four sweetening agents are included in flavoring systems of the invention. High fructose corn syrup, glycerin, saccharin sodium, monoammonium glycyrrhizinate, and acesulfame potassium are most preferred sweetening agents. Preferably, sweetening agents are included in flavoring systems of the invention in a total amount of at least about 20% by weight of the total weight of the pharmaceutical composition and not more than about 67% by weight. More preferably, sweetening agents are included in flavoring systems of the invention in a total amount of at least about 22% by weight and not greater than about 27.5% by weight. Most preferred flavoring systems of the invention comprise the following sweetening agents: high fructose corn syrup in an amount of about 16.6% by weight, glycerin in an amount of about 5.5% to about 8.5% by weight, monoammonium glycyrrhizinate in an amount of about 0.58% by weight, saccharin sodium in an amount of about 0.40% by weight; and acesulfame potassium in an amount of about 0.40% by weight. As used herein the terms "comprise(s)", "comprising", "contain(s)", "containing", "include(s)" and "including" when referencing ingredients of pharmaceutical compositions of the invention, shall refer to: (1) ingredients added individually or simultaneously with other ingredients to pharmaceutical compositions of the invention; or (2) ingredients that may be formed during preparation of pharmaceutical compositions of the invention.

The invention is also directed toward liquid, preferably orally dosed, pharmaceutical compositions comprising: (a) a flavoring system of the invention; (b) one or more pharmaceutically active agents, such as lopinavir, ritonavir, or mixtures thereof; (c) and a solvent system. Optionally, pharmaceutical compositions of the invention may also include one or more thickening agents, such as polyvinylpyrrolidone, one or more bioavailability enhancing agents, such as a castor oil derivative, one or more antioxidants, and/or preservatives.

Because, pharmaceutically active agents, such as lopinavir and ritonavir are practically insoluble in water, particular types of pharmaceutically acceptable solubilizing agents (i.e., solvents) should be included in the solvent system. These particular types of solubilizing agents include, but are not limited to: water, pharmaceutically acceptable alkyl alcohols, and pharmaceutically acceptable alkylene glycols. At least two of these particular types of solubilizing agents should be included in the solvent system, and most preferably all three of these types of agents should be included. At least about 32% by weight and not more than about 69% by weight of pharmaceutical compositions of the invention is the solvent system. More preferably, the solvent system comprises at least about 53% by weight of pharmaceutical compositions of the invention and not greater than about 60% by weight. These total amounts for the solvent system and the amounts for each of the individual solubilizing agents included in solvent systems of the invention exclude any additional amounts of solubilizing agents: (a) that are a part of other ingredients (e.g., flavored ingredients or sweetening agents) included in the composition; (b) that are used to rinse the vessel in which the pharmaceutical compositions of the invention are made as described in the "Preparation of the Pharmaceutical Compositions" section herein below; and (c) that are used to bring the final pharmaceutical composition up to batch volume as described in the "Addition of Any Bioavailabilty Enhancer and Any Additional Ingredients" section below.

It is also noted that the total amounts disclosed herein for the flavoring system and for each of the individual ingredients included in the flavoring system generally include, unless otherwise noted, any solvents or solubilizing agents that are incorporated into such individual ingredients. For example, high fructose corn syrup is a preferred sweetening agent that can be included in flavoring systems of the invention, and high fructose corn syrup usually contains a significant amount of water. The weight of the water that is included in the amounts for high fructose corn syrup is included in the total weight amounts disclosed herein for sweetening agents and flavoring systems. The amount of water included in the high fructose corn syrup is not included in the amounts disclosed herein for solubilizing agents or for the solvent system.

Preferred solubilizing agents include water, ethanol, propylene glycol, polyethylene glycol, and mixtures thereof. The most preferred alkyl alcohol is ethanol, and the most preferred alkylene glycol is propylene glycol.

Flavoring systems of the invention are generally included in an amount of at least about 20% by weight of pharmaceutical compositions of the invention and not more than about 70% by weight. More preferably, flavoring systems of the invention are included in an amount of at least about 22% by weight and not greater than about 68% by weight of the pharmaceutical compositions of the invention. Most preferably, flavoring systems of the invention are included in pharmaceutical compositions of the invention in an amount of about 27% by weight to about 29.5% by weight.

Other ingredients, such as thickening agents and agents that enhance the bioavailability of the pharmaceutically active agents may also be included in pharmaceutical compositions of the invention. The most preferred thickening agent is polyvinylpyrrolidone. The most preferred bioavailability enhancer is a castor oil derivative, such as polyoxyl 40 hydrogenated castor oil, which is commercially available as Cremophor RH40. In preferred embodiments of the invention, one or more thickening agents is included in pharmaceutical compositions of the invention in a total amount of at least about 2.5% by weight and not greater than about 5% by weight, and one or more bioavailability enhancers are included in a total amount of at least about 0.01% by weight and not greater than about 3% by weight. Most preferably, polyvinylpyrrolidone is included in pharmaceutical compositions of the invention in an amount of about 3% by weight, and the castor oil derivative is included in an amount of about 1% by weight.

Ritonavir or derivatives thereof, lopinavir or derivatives thereof, and mixtures thereof are preferably the pharmaceutically active agents included in the invention. More preferably, both ritonavir or one or more of its derivatives and lopinavir or one or more of its derivatives are included in the compositions of the invention. If both ritonavir or one or more of its derivatives and lopinavir or one or more of its derivatives are included in compositions of the invention, then most preferably, the weight ratio of the amount of lopinavir or one or more of its derivatives to ritonavir or one or more of its derivaties is about 4:1. Preferably, at least about 4% by weight of the pharmaceutical composition is one or more pharmaceutically active agents, and more preferably the amount of pharmaceutically active agent(s) in the composition is not greater than about 10% by weight of the pharmaceutical composition. If both lopinavir or one or more of its derivatives and ritonavir or one or more of its derivatives are both included in compositions of the invention, then preferably, ritonavir or one or more of its derivatives is included in the composition in an amount of at least about 1.30% by weight and not greater than about 2.10% by weight; and preferably, lopinavir or one or more of its derivatives is included in the composition in an amount of at least about 2.5% by weight and not greater than about 8% by weight. Most preferably, ritonavir or one or more of its derivatives is included in compositions of the invention in an amount of about 2% by weight, and lopinavir or one or more of its derivatives is included in compositions of the invention in an amount of about 8% by weight.

The invention is also directed toward methods of making pharmaceutical compositions of the invention. Methods of the invention include: (a) charging a vessel with at least a portion of the solvent system; (b) dissolving the one or more pharmaceutically active agents, such as ritonavir or its derivatives, lopinavir or its derivatives, or mixtures thereof in the vessel with at least a portion of the solvent system; (c) dissolving the flavor modifiers (excluding any flavor modifiers in liquid form) and any non-liquid sweetening agents in water in a separate vessel to form a side mixture; (d) and combining the side mixture with the at least a portion of the solvent system containing the one or more dissolved pharmaceutically active agents, any one or more liquid sweetening agents, any liquid flavor modifiers, the flavored ingredients, and any remaining portion of the solvent system. Methods of the invention also include combining all of the ingredients in the vessel as stated in the previous sentence without preparing a separate side mixture. Preferably, if a castor oil derivative is included in the composition, it is heated prior to being added to the vessel. If menthol crystals are used in the composition, then preferably, they are dissolved in the at least a portion of the solvent system prior to dissolution of the one or more pharmaceutically active agents in the solvent system. Preferably, the vessel has mixing means to mix the vessel contents during the process. Most preferably, a thickening agent, such as polyvinylpyrrolidone, is added to the vessel and mixed with other ingredients in the pharmaceutical composition.

DETAILED DESCRIPTION OF THE INVENTION

Generally, liquid pharmaceutical compositions of the invention include a flavoring system, at least one pharmaceutically active agent, a solvent system and optionally other additives useful in enhancing the bioavailability of and/or increasing the viscosity and/or stability of pharmaceutical compositions. Flavoring systems of the invention include at least one sweetening agent, and at least two flavored ingredients selected from the group consisting of: a menthol flavored ingredient, a peppermint flavored ingredient, a vanilla flavored ingredient, a cotton candy flavored ingredient, and mixtures thereof. Flavoring systems of the invention also include at least one flavor modifier selected from the group consisting of sodium citrate, sodium chloride, citric acid, and mixtures thereof. A solvent system in which each of the pharmaceutically active agents can dissolve is also included in pharmaceutical compositions of the invention.

As used herein, the terms below have the following meanings. The term "flavored ingredient" shall mean any compound or composition that: (a) is pharmaceutically acceptable, (b) is not a sweetening agent, and (c) imparts a known and readily identifiable blend of taste and/or smell sensations to pharmaceutical compositions of the invention. Examples of flavored ingredients include, but are not limited to: wild cherry flavor, strawberry flavor, banana flavor, peppermint flavor, peppermint oil, menthol flavor, menthol crystals, cotton candy flavor, vanilla flavor, mixed fruit flavor, and chocolate flavor. As used herein, the term "pharmaceutically acceptable" refers to a compound or composition that is currently or becomes in the future accepted by: (1) the United States Food and Drug Administration as useable in pharmaceutical compositions made and/or sold in the United States; or (2) any pharmaceutical regulatory agency outside of the United States as useable in pharmaceutical compositions made and/or sold in the jurisdiction governed by such regulatory agency.

The term "lopinavir" as used herein shall mean a pharmaceutically active agent represented by the chemical name [1S-[1R*,(R*),3R*,4R*]]-N-[4-[[(2,6-dimethylphenoxy)acetyl]amino]-3-hydroxy-5-phenyl-1-(phenylmethyl)pentyl]tetrahydro-alpha-(1-methylethyl)-2-oxo-(2H)-pyrimidine acetamide. The term "derivative(s)" as used herein when referring to lopinavir shall mean the pharmaceutically acceptable salts, esters, pharmaceutical derivatives, and pharmaceutical analogs of lopinavir as described in U.S. Pat. No. 5,914,332, which issued on Jun. 22, 1999 and is hereby incorporated by reference. The term "ritonavir" as used herein shall mean a pharmaceutically active agent represented by the chemical name [5S-(5R*,8R*,10R*,11R*)]-10-Hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid, 5-thiazolylmethyl ester. The term "derivative(s)" as used herein when referring to ritonavir shall mean the pharmaceutically acceptable salts, esters, pharmaceutical derivatives, and pharmaceutical analogs of ritonavir as described in U.S. Pat. Nos. (a) 5,541,206, which issued on Jul. 30, 1996; and (b) 5,648,497, which issued on Jul. 15, 1997 and both of which are hereby incorporated by reference.

The term "sweetening agent" shall mean any pharmaceutically acceptable liquid or solid compound or composition that is not a flavored ingredient and that has or imparts to pharmaceutical compositions a sugar-like or sugar-based taste. Examples of sweetening agents include, but are not limited to, glycerin, saccharin sodium, acesulfame potassium, monoammonium glycyrrhizinate, and high fructose corn syrup. The term "flavor modifier(s)" as used herein shall mean pharmaceutically acceptable ingredients that are not sweetening agents and not flavored ingredients that enhance the flavor of pharmaceutical compositions. Examples of flavor modifiers include, but are not limited to: sodium citrate, citric acid, and sodium chloride.

Flavoring Systems

Generally, pharmaceutical compositions with the best flavor profiles have when tasted: (1) an immediate impact of an identifiable flavor; (2) rapid development of a balanced and full flavor; (3) compatible mouthfeel factors (i.e., the composition is texturally satisfactory); (4) no "off-notes" or unexpected flavors; (5) and a short aftertaste. Applicants' goal in developing the flavoring systems of the invention was to insure that compositions containing lopinavir or its derivatives, ritonavir or its derivatives, and mixtures thereof would exhibit most, if not all of these characteristics.

In general, there are four distinct basic taste types in a flavor profile: bitter, sweet, sour, and salty. These four basic taste types are used to describe tastes of orally ingested compositions while they are in the mouth and to describe the aftertaste associated with these compositions. Lopinavir and its derivatives and ritonavir and its derivatives tend to have a flavor profile that is undesirably high in the bitter basic taste, and these pharmaceutically active agents also have a lingering aftertaste. Because these drugs without a flavoring system or with an unsatisfactory flavoring system have an undesirable flavor profile, patients are less likely to take the drug in compliance with their daily dosage regimen. Therefore, Applicants have developed a flavoring system that counteracts the undesirable aftertaste and the bitter basic taste in these drugs' flavor profiles. In addition, the flavoring system is compatible with the particular types of solvent systems required for these two drugs.

Because lopinavir and ritonavir are practically insoluble in water at room temperature and pressure (i.e., approximately 25° C. and 1 atmosphere of pressure), these drugs must be dissolved and maintained in a particular type of solvent system, and flavoring systems of the invention are compatible with such solvent systems. Generally, flavoring systems of the invention include at least two flavored ingredients, at least one sweetening agent, and at least two flavor modifiers.

Flavored Ingredients

The flavored ingredients in flavoring systems of the invention minimize the unpleasant aftertaste and counteract the bitter basic taste in the lopinavir and ritonavir (and their respective derivatives) flavor profiles. A variety of flavored ingredients can be used to improve these drugs' flavor profiles; however, Applicants have optimized these drugs' flavor profiles by including at least two flavored ingredients in their flavoring systems. Preferably, at least three flavored ingredients are included, and most preferably at least four flavored ingredients are included in flavoring systems of the invention. Applicants have found that combinations of the following flavors are particularly useful in flavoring systems for pharmaceutical compositions containing ritonavir or one or more of its derivatives, lopinavir or one or more of its derivatives, and mixtures thereof: vanilla, cotton candy, menthol, and peppermint. However, other flavors may also be used. For example, green apple, licorice, chocolate, chocolate mint, strawberry, banana, mixed fruit, and cherry may be used alone or in combination with the previously identified flavors that are useful in the invention.

Generally, flavored ingredients are included in pharmaceutical compositions of the invention in a total amount of at least about 1.4% by weight and not greater than about 3.5% by weight. Preferably, flavored ingredients are included in pharmaceutical compositions of the invention in a total amount of at least about 1.45% by weight and not greater than about 3% by weight, and more preferably in an amount of at least about 2.4% by weight and not greater than about 2.8% by weight. Most preferably, flavored ingredients are included in pharmaceutical compositions of the invention in an amount of about 2.6% by weight. Most preferred flavoring systems of the invention comprise menthol, peppermint, vanilla, and cotton candy flavored ingredients.

The menthol flavored ingredient is included in most preferred flavoring systems of the invention in any form (i.e., liquid or solid). For example, menthol crystals (i.e., in solid form) may be incorporated into compositions of the invention, or menthol crystals may be dissolved into a pharmaceutically acceptable solvent (e.g., propylene glycol) and the dissolved crystals in the solvent may be included in compositions of the invention. Preferably, the amount of menthol flavored ingredient included in most preferred flavoring systems of the invention is at least about 0.03% by weight and not greater than about 0.25% by weight. Most preferably, the menthol flavored ingredient is included in the pharmaceutical composition in an amount of about 0.05% by weight. These weight percentages exclude the weight of any solvent in which any menthol in solid form may be dissolved. Most preferably, the menthol flavored ingredient is menthol crystals. Menthol crystals that are useful in the invention are L-Menthol Crystals USP available from Takasago of Rockleigh, N.J., U.S.A.

The vanilla flavored ingredient can be included in most preferred flavoring systems of the invention in any form (i.e., liquid or solid). For example, extracts from vanilla beans (i.e., vanilla bean extract) may be included in compositions of the invention with or without a pharmaceutically acceptable solvent. Preferably, the amount of vanilla flavored ingredient (including any solvent in which vanilla been extract, for example, may be dissolved) included in most preferred flavoring systems of the invention is at least about 0.70% by weight and not greater than about 1.50% by weight, and more preferably the amount of vanilla flavored ingredient is at least about 1.15% by weight and not greater than about 1.35% by weight. Most preferably, the vanilla flavored ingredient is included in the composition in an amount of about 1.25% by weight, and most preferably, vanilla flavor is included in the pharmaceutical composition as the vanilla flavored ingredient. Two vanilla flavors that are useful in the invention are commercially available from Bush Boake & Allen, Inc. of Chicago, Ill. as Artificial Vanilla Cream Flavor and as Natural and Artificial Vanilla Flavor (#33869, Yarnalla).

The cotton candy flavored ingredient can be included in most preferred flavoring systems of the invention in any form (i.e., liquid or solid); however, Applicants are currently not aware of a solid form of a cotton candy flavored ingredient, and the liquid form is preferred. Preferably, the amount of cotton candy flavored ingredient included in most preferred flavoring systems of the invention is at least about 0.55% by weight and not greater than about 1.10% by weight, and more preferably the amount of cotton candy flavored ingredient is at least about 0.95% by weight and not greater than about 1.05% by weight. Most preferably, the cotton candy flavored ingredient is included in the pharmaceutical composition in an amount of about 1.00% by weight, and most preferably, the cotton candy flavored ingredient is cotton candy flavor. A cotton candy flavor that is useful in the invention is commercially available from E.A. Weber & Co. of Wheeling, Ill. as Artificial Cotton Candy Flavor #30-92-0011.

The peppermint flavored ingredient can be included in most preferred flavoring systems of the invention in any form (i.e., liquid or solid). Preferably, the amount of peppermint flavored ingredient included in most preferred flavoring systems of the invention is at least about 0.15% by weight and not greater than about 0.60% by weight, and more preferably the amount of peppermint flavored ingredient is at least about 0.25% by weight and not greater than about 0.35% by weight. Most preferably, the peppermint flavored ingredient is included in the pharmaceutical composition in an amount of about 0.30% by weight, and most preferably the peppermint flavored ingredient is peppermint oil. One peppermint oil that is useful in the invention is commercially available from A.M. Todd Co. of Kalamazoo, Mich. as Peppermint Oil NF Type 102-130.

It is noted that many flavored ingredients are commercially available in two forms: solids and liquids and that the liquids are available in various potencies. It is also noted that both forms of these ingredients may be diluted with starches, maltodextrin, gums, and other diluents known in the flavoring agent art and that the flavored ingredients in liquid form may also be diluted with pharmaceutically acceptable solvents. The weight percentages associated with the flavored ingredients herein pertain to flavored ingredients in a dry or liquid form, unless otherwise noted, having a potency that is pharmaceutically equivalent to the potency of the pharmaceutically acceptable commercially available flavored ingredients cited herein.

Sweetening Agents

In order to improve the flavor profile of pharmaceutical compositions containing pharmaceutically active agents, such as ritonavir or its derivatives and lopinavir or its derivatives, at least one sweetening agent should be included in the composition and preferably at least two sweetening agents should be included. More preferably, at least three or four sweetening agents should be included and most preferably at least five sweetening agents should be included in flavoring systems of the invention. Examples of useful sweetening agents include, but are not limited to: glycerin, monoammonium glycyrrhizinate, high fructose corn syrup, saccharin sodium, acesulfame potassium, maltitol, sucrose, sorbitol, hydrogenated starch hydrolysate, mannitol, xylitol, erythritol, maltose, dextrose, and fructose, and mixtures thereof.

Sweetening agents useful in the invention can be included in compositions of the invention in any form (i.e., liquid or solid).

Preferably, the total amount of sweetening agent(s) included in compositions of the invention is at least about 20% by weight and not greater than about 67% by weight. More preferably at least about 22% by weight and not greater than about 28% by weight of the pharmaceutical compositions is sweetening agent(s). In most preferred flavoring systems of the invention, the total amount of sweetening agents is at least about 23% by weight and not greater than about 27% by weight. It is noted that the sweetening agent weight percentages detailed herein exclude any sweetening agents used as solvents in any one or more flavored ingredients.

In most preferred flavoring systems of the invention, the at least five sweetening agents included in the composition are glycerin, high fructose corn syrup, monoammonium glycyrrhizinate, acesulfame potassium, and saccharin sodium. Preferably, the amount of glycerin included in most preferred flavoring systems of the invention is at least about 5% by weight and not greater than about 30% by weight, and more preferably the amount of glycerin is at least about 5.25% by weight and not greater than about 28.5% by weight. Most preferably, glycerin is included in pharmaceutical compositions of the invention in an amount of at least about 5.85% by weight and not greater than about 8.5% by weight. Two glycerin products that are useful in the invention are commercially available from Dial of Montgomery, Ill., U.S.A and Witco of Memphis, Tenn., U.S.A. as Glycerin USP and Kemstrene 99.7% USP respectively.

High fructose corn syrup is preferably included in most preferred flavoring systems of the invention in an amount of at least about 14.5% by weight and not greater than about 33.6% by weight, and more preferably in an amount of at least about 15.7% by weight and not greater than about 17.4% by weight. Most preferably, high fructose corn syrup is included in pharmaceutical compositions of the invention in an amount of about 16.6% by weight. A high fructose corn syrup that is useful in the invention is commercially available as Hi-Sweet 55 Code 352 from Roquette of Keokuk, Iowa, U.S.A.

Preferably, the amount of acesulfame potassium included in most preferred flavoring systems of the invention is at least about 0.35% by weight and not greater than about 0.85% by weight, and more preferably at least about 0.35% by weight and not greater than about 0.45% by weight. Most preferably, acesulfame potassium is added to the pharmaceutical composition in an amount of about 0.40% by weight. An acesulfame potassium product that is useful in the invention is commercially available from Nutrinova Inc. of Somerset, N.J. as Sunett pharmaceutical grade acesulfame potassium, FCC.

Saccharin sodium is included in most preferred flavoring systems of the invention in an amount of at least about 0.05% by weight and not greater than about 0.85% by weight, and more preferably in an amount of at least about 0.35% by weight and not greater than about 0.45% by weight. Most preferably, saccharin sodium is included in the pharmaceutical composition in an amount of about 0.40% by weight. Saccharin sodium that is useful in the invention is commercially available from Syncal S of Cincinnati, Ohio, U.S.A. as Sodium Saccharin Powder USP/NF. As used herein the terms "USP" or "USP/NF" mean United States Pharmacopoeia and National Formulary, and the reference indicates that the ingredient meets the appropriate United States Pharmacopoeia and National Formulary standards or specifications.

Monoammonium glycyrrhizinate is included in most preferred flavoring systems of the invention in an amount of at least about 0.35% by weight and not greater than about 0.65% by weight, and more preferably in an amount of at least about 0.55% by weight and not greater than about 0.65% by weight. Most preferably, monoammonium glycyrrhizinate is included in the pharmaceutical composition in an amount of about 0.58% by weight. Monoammonium glycyrrhizinate can be included in compositions of the invention in liquid or solid form. One example of a useful commercially available liquid form of monoammonium glycyrrhizinate are the magnasweet products, which are commercially available from MacAndrews & Forbes of Camden, N.J., U.S.A. One product that is useful in particular is Magnasweet 110 2X, which is monoammonium glycyrrhizinate dissolved in glycerin. This particular product is 20% by weight monoammonium glycyrrhizinate and 80% by weight glycerin based upon the total weight of the magnasweet composition. If such a magnasweet product is used as a sweetening agent in compositions of the invention, then products that are 20% by weight monoammonium glycyrrhizinate should be included in most preferred flavoring systems of the invention in an amount of at least about 1.60% by weight and not greater than about 3.10% by weight, and more preferably in an amount of at least about 2.75% by weight and not greater than about 3.10% by weight. Most preferably, such a magnasweet product is included in the pharmaceutical composition in an amount of about 2.90% by weight.

Flavor Modifiers

At least one other ingredient should be included in flavoring systems of the invention. Generally, these ingredients are flavor modifiers. Generally, flavor modifiers are included in flavoring systems for pharmaceutical compositions in order to enhance, extend or accentuate flavored ingredients and/or sweetening agents. Flavor modifiers tend to facilitate a higher initial flavor impact, to extend the effect of flavors and sweeteners well into the aftertaste, and to combat the lingering effects of bitter and other undesirable aftertaste characteristics originating from the pharmaceutically active ingredients or solubilizing agents included in the pharmaceutical composition.

In order to improve the flavor profile of pharmaceutical compositions containing pharmaceutically active agents, such as ritonavir or its derivatives and lopinavir or its derivatives, at least one flavor modifier should be included in the composition and preferably at least two flavor modifiers should be included in compositions of the invention. Most preferably, at least three flavor modifiers are included in flavoring systems of the invention. Examples of useful flavor modifiers include, but are not limited to: sodium citrate, sodium chloride, citric acid, thaumatin, and mixtures thereof.

Preferably, flavor modifiers are included in compositions of the invention in an amount of at least about 0.10% by weight and not greater than about 1.00% by weight. More preferably flavor modifiers are included in compositions of the invention in an amount of at least about 0.60% by weight and not greater than about 0.70% by weight. Most preferably, flavor modifiers are included in compositions of the invention in an amount of about 0.66% by weight.

In most preferred flavoring systems of the invention, the at least three flavor modifiers included in the composition are citric acid, sodium chloride, and sodium citrate. Preferably, the amount of sodium citrate included in most preferred flavoring systems of the invention is not greater than about 0.25% by weight, and more preferably at least about 0.15% by weight and not greater than about 0.25% by weight. Most preferably, sodium citrate is included in the pharmaceutical composition in an amount of about 0.20% by weight. A sodium citrate product that is useful in the invention is Sodium Citrate Dihydrate USP FCC commercially available from ADM Southport of Southport, N.C., U.S.A.

Sodium chloride is preferably included in most preferred flavoring systems of the invention in an amount of not greater than about 0.40% by weight, and more preferably in an amount of at least about 0.30% by weight and not greater than about 0.40% by weight. Most preferably, sodium chloride is included in pharmaceutical compositions of the invention in an amount of about 0.35% by weight. A sodium chloride product that is useful in the invention is commercially available from Morton Salt Company of Rittman, Ohio, U.S.A. as Sodium Chloride USP.

Preferably, the amount of citric acid included in most preferred flavoring systems of the invention is at least about 0.10% by weight and not greater than about 0.25% by weight, and more preferably at least about 0.10% by weight and not greater than about 0.12% by weight. Most preferably, citric acid is included in the pharmaceutical composition in an amount of about 0.11% by weight. A citric acid product that is useful in the invention is Citric Acid USP Anhydrous Powder #0703064 commercially available from A.E. Staley of Dayton, Ohio, U.S.A.

Pharmaceutically Active Agents

Pharmaceutically active agents that are practically insoluble in water for example, ritonavir, derivatives of ritonavir, lopinavir, derivatives of lopinavir, or mixtures thereof are useful in compositions of the invention. Generally, pharmaceutical compositions of the invention are liquid in form, and preferably are orally dosed. At least one pharmaceutically active agent is included in compositions of the invention, and preferably two pharmaceutically active agents are included.

Any pharmaceutically effective and pharmaceutically acceptable amount of the pharmaceutically active agents or mixtures thereof can be included in compositions of the invention. In preferred embodiments, the total amount of pharmaceutically active agent(s) included in compositions of the invention is at least about 4% by weight and not greater than about 10% by weight. More preferably, the total amount of pharmaceutically active agent(s) included in compositions of the invention is at least about 9.5% by weight and not greater than about 10% by weight. Most preferably, the total amount of pharmaceutically active agent(s) included in compositions of the invention is about 9.8% by weight. Lopinavir, ritonavir, and/or mixtures thereof are the most preferred pharmaceutically active agents included in compositions of the invention. However, derivatives of lopinavir, derivatives of ritonavir and/or mixtures thereof are also useful in compositions of the invention. In most preferred embodiments of the invention, the ratio of lopinavir or its derivatives to ritonavir or its derivatives in pharmaceutical compositions of the invention is about 4:1 based upon the percent by weight of each agent in the composition.

If both lopinavir or its derivatives and ritonavir or its derivatives are included in the composition, then ritonavir or its derivatives are preferably included in an amount of at least about 1.30% by weight and not greater than about 2.10% by weight; and lopinavir or its derivatives are included in an amount of at least about 2.50% by weight and not greater than about 8.0% by weight based upon the total weight of the pharmaceutical composition. Lopinavir or its derivatives are most preferably included in compositions of the invention in an amount of about 8% by weight, and ritonavir or its derivatives are most preferably included in an amount of about 2% by weight based upon the total weight of the pharmaceutical composition.

Solvent Systems

The low aqueous solubilities and insufficient bioavailability of ritonavir and lopinavir in their solid forms create a formulation challenge for developing pharmaceutical compositions containing one or both of these drugs or their respective derivatives, especially in instances when the total daily dose is relatively high. In general, lopinavir is adequately soluble at room temperature (i.e., about 25° C.) in pharmaceutically acceptable solvents, such as propylene glycol and ethanol. However, ritonavir is only poorly or moderately soluble in these types of pharmaceutically acceptable solvents. Therefore, individual solvents may not provide sufficient solubility for pharmaceutical compositions containing both of these pharmaceutically active agents or their respective derivatives. Applicants have found that the solubilities of both ritonavir and lopinavir and their respective derivatives are significantly improved in a co-solvent system, which indicates a synergistic effect when more than one solvent is used in the solvent system.

Applicants have discovered that at least two and preferably at least three types of pharmaceutically acceptable solubilizing agents are useful in solvent systems included in pharmaceutical compositions of the invention. These solubilizing agents are pharmaceutically acceptable water, alkyl alcohols, and alkylene glycols. Other types of pharmaceutically acceptable solubilizing agents can be useful in solvent systems of the invention. Generally, any pharmaceutically acceptbale solubilizing agent that is useful in increasing the solubility of ritonavir and/or lopinavir and/or their respective derivatives is useful as a solubilizing agent in solvent systems of the invention. Examples of useful solubilizing agents include, but are not limited to: ethanol, propylene glycol, polyethylene glycol, fractionated coconut oil, mixtures thereof, and all other pharmaceutically acceptable solvents disclosed in U.S. Pat. Nos. 4,484,801 and 5,914,332, which are incorporated herein by reference.

Preferably, the solvent system is at least about 32% by weight and not greater than about 69% by weight of the total weight of the pharmaceutical composition. More preferably, at least about 53% by weight and not greater than about 60% by weight of the pharmaceutical composition is the solvent system.

In most preferred pharmaceutical compositions of the invention, the at least three solubilizing agents included in the pharmaceutical composition comprise water, propylene glycol, and ethanol. The amount of water included in most preferred solvent systems of the invention is not greater than about 8.5% by weight, and more preferably at least about 6% by weight and not greater than about 8% by weight. Most preferably, water is included in the most preferred pharmaceutical compositions in an amount of about 6.80% by weight. These weight percentages for water pertain only to the amount of water that is added to the composition and do not include any water that is generated during preparation of the pharmaceutical composition. Water that is useful in the invention is pharmaceutically acceptable purified and distilled water and any water that is generated during preparation of the pharmaceutical composition.

Any type of pharmaceutically acceptable alkyl alcohol can be included in solvent systems of the invention. Preferably, the one or more alkyl alcohols included in pharmaceutical compositions of the invention are included in an amount of at least about 24% by weight and not greater than about 42% by weight, and more preferably in the amount of at least about 33% by weight and not greater than about 37% by weight. Most preferably, one or more alkyl alcohols are included in compositions of the invention in an amount of about 35% by weight. Additional amounts of an alkyl alcohol, such as ethanol, can be included in compositions of the invention to obtain the proper dosage form. Ethanol is the most preferred alkyl alcohol for use in compositions of the invention. An ethanol that is useful in the invention is Alcohol, Dehydrated, USP 200 Proof (reagent grade, non-beverage) commercially available from Equistar of Tuscola, Ill., U.S.A. An alkyl alcohol of 190 proof may be used by proportionally reducing the amount of added water.

Although any type of pharmaceutically acceptable alkylene glycol can be included in preferred solvent systems of the invention, propylene glycol is most preferred. Preferably one or more pharmaceutically acceptable alkylene glycols are included in an amount of at least about 7.5% by weight and not greater than about 18% by weight, and more preferably at least about 14% by weight and not greater than about 16% by weight. Most preferably, one or more alkylene glycols are included in the pharmaceutical composition in an amount of about 15% by weight. Propylene glycol products that are useful in the invention are commercially available from Dow Chemical North America's Texas Operation in Freeport, Tex., U.S.A. and the Lyondell Bayport Plant in Pasedena, Tex. as Propylene Glycol USP.

Other Additives to the Pharmaceutical Compositions

Generally, other pharmaceutically acceptable additives, such as thickening agents, bioavailability enhancers, antioxidants, and/or preservatives, may be included in compositions of the invention. Preferably, a thickening agent is included in compositions of the invention in an amount of at least about 2.50% and not greater than about 5.0% by weight. More preferably, the amount of thickening agent that is included in compositions of the invention is at least about 2.50% by weight and not greater than about 3.20% by weight, and most preferably a thickening agent is included in the composition in an amount of about 3.0% by weight.

Any type of pharmaceutically acceptable thickening agent is useful in the invention. These types of thickening agents include, but are not limited to: polyvinylpyrrolidone, carbomers, xanthan gum, hydrated magnesium aluminum silicates, and cellulose derivatives, such as carboxymethyl cellulose. Most preferably, polyvinylpyrrolidone is used in the compositions of the invention. A useful polyvinylpyrrolidone is polyvinylpyrrolidone USP, which is commercially available from ISP Chemicals of Texas City, Tex., U.S.A. as Plasdone K 29/32.

Preferably, a pharmaceutically acceptable bioavailability enhancer is included in compositions of the invention in an amount of not greater than about 3% by weight. More preferably, the amount of bioavailability enhancer included in the composition is at least about 0.95% and not greater than about 1.10%, and most preferably the bioavailability enhancer is included in the composition in an amount of about 1.0% by weight.

Any type of pharmaceutically acceptable bioavailability enhancer is useful in the invention. These types of bioavailability enhancers include, but are not limited to: polyoxyethyleneglycerol triricinoleate, castor oil derivatives, such as but not limited to polyoxyethylene glycol 40 hydrogenated castor oil, polyoxyethylene (20) sorbitan monooleate, sorbitan fatty acid esters, polyoxyethylene sorbitan fatty acid esters (i.e., polysorbate), and mixtures thereof. Most preferably, polyoxyl 40 hydrogenated castor oil USP, which is commercially available as Cremophor RH40 from BASF of Mt. Olive, N.J., U.S.A. is used in compositions of the invention.

The following is the most preferred pharmaceutical composition of the invention.

| Ingredient | % By Weight |
| --- | --- |
| Menthol Crystals | 0.05 |
| Peppermint Oil | 0.30 |
| Vanilla Flavor | 1.25 |
| Cotton Candy Flavor | 1.00 |
| Sodium Chloride | 0.35 |
| Sodium Citrate | 0.20 |
| Citric Acid | 0.11 |
| Water (excluding generated water) | 6.80 |
| Ethanol | 35.00 |
| Propylene Glycol | 15.00 |
| Saccharin Sodium | 0.40 |
| Acesulfame Potassium | 0.40 |
| High Fructose Corn Syrup | 16.57 |
| Glycerin | 8.17 |
| Monoammonium Glycyrrhizinate | 0.58 |
| Polyoxyl 40 Hydrogenated Castor Oil | 1.00 |
| Ritonavir | 1.97 |
| Lopinavir | 7.86 |
| Polyvinylpyrrolidone | 3.00 |

Preparation of the Pharmaceutical Compositions

Generally, pharmaceutical compositions of the invention may be prepared in any pharmaceutically acceptable manner in which all ingredients are satisfactorily dissolved in the composition. In general, Applicants have found that for the most efficient production any one or more solubilizing agents included in the solvent system should be added to the mixing vessel first and any one or more heated semi-solids or heated viscous liquids, such as any castor oil derivatives, should be the ingredients added last or at least near the end of the process. In addition, the most insoluble solids included in the composition, such as any menthol crystals and/or the pharmaceutically active agents (e.g., ritonavir and/or lopinavir), should be added to the vessel just after any one or more solubilizing agents; and any one or more flavored ingredients in a non-solid form should be added to the mixing vessel just before any of the heated semi-solids or heated viscous liquids. Applicants have also found that continuous mixing between the addition of ingredients facilitates complete dissolution of all the ingredients included in the composition.

In preferred methods, Applicants have found that pharmaceutical compositions of the invention can be prepared by: (1) charging a vessel with at least a portion of the solvent system; (2) dissolving any menthol crystals or any other menthol in solid form in the portion of the solvent system that is in the vessel; (3) dissolving the pharmaceutically active agent(s) in the vessel containing the solvent system; (4) dissolving any thickening agent in the vessel containing the solvent system and pharmaceutically active agent(s); (5) dissolving the water soluble non-liquid flavoring system ingredients, excluding the flavored ingredients, in water to form a side mixture; (6) adding the side mixture, any one or more liquid sweetening agent(s) and other liquid flavoring system ingredients, the flavored ingredients, and any remaining excipients to the mixing vessel containing the dissolved pharmaceutically active agent(s).

Charging a Vessel with Solubilizing Agents

Any one or more solubilizing agents included in the solvent system should first be added to a mixing vessel. Preferably, the mixing vessel is a jacketed stainless steel pressure rated vessel having the ability to continuously mix the composition during the preparation process. Mixing is preferably performed at one or more speeds of 100-320 revolutions per minute ("rpm") with two hydrofoil impellers that are secured to the mixing vessel. Preferably, the mixing vessel is capable of being purged with Nitrogen, NF, to minimize any explosion or fire hazards. More preferably, a continuous flow of nitrogen is applied to the vessel during the preparation of compositions of the invention. After all the ingredients are added to the vessel as fully described below, the vessel should be sealed and a nitrogen head pressure of at least 1 psig should be maintained after the vessel is sealed. Examples of mixing vessels that can be used to make pharmaceutical compositions of the invention are: an 800L stainless steel tank available from Northern Stainless, Inc. of Tomahawk, Wis.; and a 1900L stainless steel tank available from Brighton Corp. of Cincinnati, Ohio.

Any one or more solubilizing agents used in the composition should be added to the vessel first so that the remaining ingredients can be dissolved in these agents. Preferably, water, an alkyl alcohol (e.g., ethanol), and an alkylene glycol (e.g., propylene glycol) are solubilizing agents that are first added to the vessel with continuous mixing at a speed of 100-320 rpm and continuous nitrogen flow as described above. The solubilizing agents should be added to the mixing vessel at a temperature of about 25° C., and should be mixed until there is no visible separation of the solvent system in the vessel.

Dissolution of Any Menthol in Solid Form

Because any menthol in solid form (e.g., crystals) has low solubility in water, it preferably is added to the mixing vessel and dissolved in the solvent system just after the solubilizing agents are mixed in the vessel. After any menthol is added to the vessel at a temperature of about 25° C., the contents of the vessel should be mixed until the menthol is dissolved. Typically, the menthol and solubilizing agents should be mixed for at least about 5 minutes prior to adding the pharmaceutically active agents to the vessel. Any menthol included in the composition of the invention in liquid from may be added to the vessel with the flavored ingredients as described herein below.

Dissolution of the Pharmaceutically Active Agent(s)

Prior to adding any one or more pharmaceutically active agents, the mixing vessel temperature must be set at about 25° C., and the temperature of the vessel's contents should be at least about 18° C. and not greater than about 30° C. This temperature range should be maintained throughout the remainder of the preparation process. Preferably, if both ritonavir or its derivatives and lopinavir or its derivatives are included in the composition, then ritonavir or its derivatives should be slowly and steadily added to the mixing vessel and mixed, and then lopinavir or its derivatives should be added to the vessel in the same manner. In order to facilitate dispersion and dissolution of these pharmaceutically active agents, the vessel contents should be mixed continuously at a speed of about 200-320 rpm so that a vortex is maintained in the vessel. Generally, after any thickening agents are added to the vessel, as described below, the mixing speed may be lowered without causing any significant amount of the pharmaceutically active agents to settle on the bottom of the vessel.

Preferably, after the pharmaceutically active agents are added to the vessel, the vessel walls and any hopper or port through which the pharmaceutically active agents were added are rinsed with a pharmaceutically acceptable alkyl alcohol, such as ethanol, to insure that all the pharmaceutically active agent(s) is washed into and dissolved in the vessel. To equalize the solution compositions for each batch size, an alcohol rinse of 5.0% by weight per unit volume of the pharmaceutical composition for an 800 liter batch size and an alcohol rinse of about 14.4% by weight per unit volume of the composition for a 2000 liter batch size should be used to rinse the walls and any hopper or ports of the mixing vessel. Preferably, after the walls and hopper or any port through which any one or more pharmaceutically active agents were delivered are rinsed, each batch contains about 31% by weight per unit volume of the composition of an alkyl alcohol, such as ethanol. Continuous mixing and re-circulation of the vessel contents help to insure that a minimal amount of solids settle to the bottom of the vessel and that the dissolution of the pharmaceutically active agents is complete. Once dissolution of the pharmaceutically active agents is confirmed by visual inspection and/or sampling from the vessel's bottom, then any thickening agent(s) and other solid low- or non-water soluble ingredients should be added to the vessel.

Dissolution of Any Thickening Agent(s) and Other Dry Solids

Any remaining dry solid low- or non-water soluble ingredients, such as any thickening agents, should be added to and uniformly mixed in the vessel after the pharmaceutically active agent(s). Any thickening agent(s) or other low- or non-soluble ingredients included in the composition should be added slowly and steadily to the vessel to facilitate its complete dispersion and dissolution. A directional funnel can be used during the addition of these ingredients (e.g., any thickening agent) to minimize any clumping, agglomeration and adherence to the vessel walls. The vessel contents should be mixed until the ingredients are uniformly mixed.

Addition of Any Liquid Sweetening Agents

Preferably, any one or more liquid sweetening agents are added to the vessel after any thickening agents or other low- or non-soluble ingredients. More preferably, if both high fructose corn syrup and glycerin are used in the composition, then the glycerin is added to the vessel before the high fructose corn syrup. After the addition of any glycerin, the contents of the vessel should be mixed until the contents are uniformly mixed, and then any high fructose corn syrup should be added to the vessel. Preferably, the high fructose corn syrup is pumped into the vessel and then mixed until the vessel contents are uniform.

Preparation and Addition of Any Side Mixture

While the vessel contents are being mixed, the water soluble powdered ingredients, except for any thickening agents, to be included in the composition preferably are dissolved in water in a separate vessel. Preferably, each of the individual water soluble powdered ingredients included in the separate vessel is less than about 3% by weight of the total pharmaceutical composition. Preferably, the separate vessel is a stainless steel vessel having continuous mixing means and the capability to mix its contents at a rate of about 650+/− 150 rpm. Any type of mixing means can be used as long as it can efficiently dissolve the water soluble ingredients in the separate vessel; however, an air mixer with one propeller is most preferred. The water soluble powdered ingredients to be included in any side mixture are the non-liquid flavor modifiers and the non-liquid sweetening agents. In most preferred compositions of the invention, the dry forms of sodium chloride, sodium citrate, saccharin sodium, acesulfame potassium, and citric acid are dissolved in water and mixed in the separate vessel to form the side mixture. These ingredients can be added to the separate vessel in any order as long as each is uniformly mixed prior to the side mixture being added to the main mixing vessel. The side mixture is prepared at ambient temperature (i.e., about 25° C.) with constant mixing at a speed of 650+/−150 rpm. In general, the vessel mix speeds should be adjusted to insure that there is a minimal amount of splash in the vessel.

Each of these powdered water soluble ingredients is preferably separately added to the side mixture and dissolved. Once the side mixture is prepared, it is preferably pumped into the main mixing vessel through the same port or transfer lines as was pumped any one or more liquid sweetening agents so that any remaining high fructose corn syrup or other liquid sweetening agents can be washed into the main mixing vessel and mixed.

Addition of the Flavored Ingredients

After the side mixture is added to the main mixing vessel, the flavored ingredients should be added to and mixed in the vessel. The flavored ingredients can generally be added in any order. In most preferred embodiments, peppermint oil, vanilla flavor, and cotton candy flavor are all added to the main mixing vessel separately and mixed in the vessel. Any menthol in liquid form or flavor modifiers in liquid form may also be added to the vessel with the flavored ingredients.

Addition of Any Bioavailability Enhancer and Any Additional Ingredients

If a bioavailability enhancer is included in the composition, it is preferably added to the mixing vessel after the flavored ingredients. More preferably, any bioavailability enhancer is added to the mixing vessel in liquid form. Thus, if a bioavailability enhancer, such as a castor oil derivative is used, it preferably is heated prior to being added to the mixing vessel. In most preferred embodiments, Polyoxyl 40 Hydrogenated Castor Oil, NF is heated in a separate vessel to a temperature of about 40° C. and melted to form a viscous liquid prior to being added to the mixing vessel. Melting any castor oil derivative prior to adding it to the mixing vessel facilitates efficient and complete dispersion and dissolution of the castor oil derivative (or any bioavailability enhancer in solid or semisolid form). Once melted, any bioavailability enhancer should be added to the main mixing vessel and mixed until the contents are uniform. Any bioavailability enhancer that does not need to be heated (i.e., in non-viscous liquid form) may be added with other non-viscous liquids earlier in the preparation process.

After any bioavailability enhancer is added to the mixing vessel and mixed, any final excipients can be added to the mixing vessel. Once all of the excipients are added to the vessel, then an additional quantity of a pharmaceutically acceptable alkyl alcohol, such as ethanol, can be added to the vessel in an amount of quantum sufficia (QS) to manufacture the final composition and batch volume. Once a sufficient amount of such an alcohol is added, the tank can be sealed and pressurized to at least 1 psig with Nitrogen, NF, and the solution can be stored at ambient temperature (i.e., about 25° C.) with continuous mixing at about 80-240 rpm.

It is appreciated that the above described steps can be performed in any order that allows each ingredient to be mixed and dissolved in the composition soon after such ingredient is added to the mixing vessel. For example, any one or more of the solubilizing agents can be added initially to the vessel followed by any one or more non-liquid ingredients, and then additional solubilizing agents can be added to the vessel. In addition, a side mixture does not have to be separately prepared as long as the water soluble powdered ingredients are added to the vessel in a pharmaceutically acceptable manner to facilitate complete dispersion and dissolution of these ingredients. By way of example, the following order of addition of the most preferred ingredients is useful to prepare pharmaceutical compositions of the invention as long as the vessel contents are continuously mixed, and each ingredient is uniformly mixed.

Adding the water to the alkyl alcohol (e.g., ethanol) in the mixing vessel

Adding any citric acid to the vessel

Adding any alkylene glycol, such as propylene glycol to the vessel

Adding a first pharmaceutically active agent, such as ritonavir, to the mixing vessel Adding any second pharmaceutically active agent, such as lopinavir, to the mixing vessel Adding a first liquid sweetening agent, such as high fructose corn syrup, to the mixing vessel Adding any menthol to the mixing vessel Adding any acesulfame potassium to the mixing vessel Adding any sodium chloride to the mixing vessel Adding any sodium saccharin to the mixing vessel Adding any sodium citrate to the mixing vessel Adding any thickening agents, such as polyvinyl pyrrolidone, to the mixing vessel Adding monoammonium glycyrrhizinate to the mixing vessel Adding peppermint oil to the mixing vessel Adding vanilla flavor to the mixing vessel Adding cotton candy flavor to the mixing vessel Adding any bioavailability enhancers, such as a castor oil derivative, (preferably in liquid form) to the mixing vessel Adding any second liquid sweetening agent, such as glycerin, to the mixing vessel In most preferred embodiments of the invention, pharmaceutical compositions of the invention are filtered prior to being put into final package form. Preferably, Buchner Filters on the order of 10-60 microns are used to filter these compositions. Most preferably, a 14 micron filter is used to filter these compositions.

The foregoing is merely illustrative of the invention and is not intended to limit the invention to the disclosed compounds, methods, and compositions. Variations and changes that are obvious to one skilled in the art are intended to be within the scope and nature of the invention, which is defined in the claims below.

What is claimed is:

1. A liquid pharmaceutical composition comprising:
    (a) a flavoring system comprising
        (i) citric acid,
        (ii) sodium citrate,
        (iii) sodium chloride,
        (iv) a menthol flavored ingredient,
        (v) a peppermint flavored ingredient,
        (vi) a vanilla flavored ingredient,
        (vii) a cotton candy flavored ingredient
        (viii) glycerin,
        (ix) monoammonium glycyrrhizinate,
        (x) saccharin sodium,
        (xi) acesulfame potassium, and
        (xii) high fructose corn syrup; and
    (b) one or more pharmaceutically active agents selected from the group consisting of ritonavir or derivatives thereof, lopinavir or derivatives thereof, and mixtures thereof.

2. The liquid pharmaceutical composition of claim 1 further comprising a solvent system comprising water, alkyl alcohols, and alkylene glycols, wherein said solvent system is present in an amount of between about 32% by weight and about 69% by weight based upon the total weight of the pharmaceutical composition.

3. The liquid pharmaceutical composition of claim 2, wherein the solvent system comprises not greater than 8.5 weight percent water, at least about 24 weight percent but not greater than 42 weight percent ethanol and at least about 7.5 weight percent but not greater than about 18 weight percent propylene glycol, based on the total weight of the pharmaceutical composition.

4. The liquid pharmaceutical composition of claim 1, wherein the flavoring system is present in an amount of between about 20% by weight and about 70% by weight based upon the total weight of the pharmaceutical composition.

5. The liquid pharmaceutical composition of claim 1, wherein the one or more pharmaceutically active agents are present in an amount of between about 4% and about 10% by weight based upon the total weight of the pharmaceutical composition.

6. The liquid pharmaceutical composition of claim 1, further comprising one or more pharmaceutically active agents in an amount of about 10% by weight based upon the total weight of the pharmaceutical composition.

7. The liquid pharmaceutical composition of claim 1, wherein the one or more pharmaceutically active agents is ritonavir.

8. The liquid pharmaceutical composition of claim 7, further comprising a solvent system comprising water, alkyl alcohols, and alkylene glycols, wherein said solvent system is present in an amount of between about 32% by weight and about 69% by weight based upon the total weight of the pharmaceutical composition.

9. The liquid pharmaceutical composition of claim 7 wherein components (i)-(xii) are present in the following weight percentages, based on the total weight of the pharmaceutical composition:
   (i) citric acid: from about 0.10 to about 0.25 weight percent,
   (ii) sodium citrate: not greater than about 0.25 weight percent,
   (iii) sodium chloride: not greater than about 0.40 weight percent,
   (iv) menthol flavored ingredient: from about 0.03 to about 0.25 weight percent,
   (v) peppermint flavored ingredient: from about 0.15 to about 0.60 weight percent,
   (vi) vanilla flavored ingredient: from about 0.70 to about 1.5 weight percent,
   (vii) cotton candy flavored ingredient: from about 0.55 to about 1.10 weight percent,
   (viii) glycerin: from about 5 to about 30 weight percent,
   (ix) monoammonium glycyrrhizinate: from about 0.35 to about 0.65 weight percent,
   (x) saccharin sodium: from about 0.05 to about 0.85 weight percent,
   (xi) acesulfame potassium: from about 0.35 to about 0.85 weight percent, and
   (xii) high fructose corn syrup: from about 14.5 to about 33.6 weight percent.

10. The liquid pharmaceutical composition of claim 1, wherein the one or more pharmaceutically active agents is a mixture of lopinavir and ritonavir.

11. The liquid pharmaceutical composition of claim 10 wherein components (i)-(xii) are present in the following weight percentages, based on the total weight of the pharmaceutical composition:
   (i) citric acid: from about 0.10 to about 0.25 weight percent,
   (ii) sodium citrate: not greater than about 0.25 weight percent,
   (iii) sodium chloride: not greater than about 0.40 weight percent,
   (iv) menthol flavored ingredient: from about 0.03 to about 0.25 weight percent,
   (v) peppermint flavored ingredient: from about 0.15 to about 0.60 weight percent,
   (vi) vanilla flavored ingredient: from about 0.70 to about 1.5 weight percent,
   (vii) cotton candy flavored ingredient: from about 0.55 to about 1.10 weight percent,
   (viii) glycerin: from about 5 to about 30 weight percent,
   (ix) monoammonium glycyrrhizinate: from about 0.5 to about 0.65 weight percent,
   (x) saccharin sodium: from about 0.05 to about 0.85 weight percent,
   (xi) acesulfame potassium: from about 0.35 to about 0.85 weight percent, and
   (xii) high fructose corn syrup: from about 14.5 to about 33.6 weight percent.

12. The pharmaceutical composition of claim 11, wherein
   (a) ritonavir is present in an amount of about 2% by weight based upon the total weight of the pharmaceutical composition; and
   (b) lopinavir is present in an amount of about 8% by weight based upon the total weight of the pharmaceutical composition.

13. The pharmaceutical composition of claim 11, wherein the peppermint flavored ingredient is peppermint oil in an amount of about 0.30% by weight; wherein the menthol flavored ingredient is menthol crystals in an amount of about 0.05% by weight; wherein the vanilla flavored ingredient is vanilla flavor in an amount of about 1.25% by weight; and wherein the cotton candy flavored ingredient is cotton candy flavor in an amount of about 1.00% by weight; and wherein all amounts by weight are based upon the total weight of the pharmaceutical composition.

14. The pharmaceutical composition of claim 11 wherein the ritonavir is present in an amount of between about 1.30% by weight and about 2.10% by weight based upon the weight of the pharmaceutical composition.

15. The pharmaceutical composition of claim 14, wherein the ritonavir is present in an amount of about 2% by weight based upon the weight of the pharmaceutical composition.

16. The liquid pharmaceutical composition of claim 11, wherein the lopinavir is present in an amount of between about 2.50% by weight and about 8% by weight based upon the total weight of the pharmaceutical composition.

17. The liquid pharmaceutical composition of claim 1, wherein the one or more pharmaceutically active agents comprises derivatives of lopinavir.

18. The liquid pharmaceutical composition of claim 17 wherein components (i)-(xii) are present in the following weight percentages, based on the total weight of the pharmaceutical composition:
   (i) citric acid: from about 0.10 to about 0.25 weight percent,
   (ii) sodium citrate: not greater than about 0.25 weight percent,
   (iii) sodium chloride: not greater than about 0.40 weight percent,
   (iv) menthol flavored ingredient: from about 0.03 to about 0.25 weight percent, (v) peppermint flavored ingredient: from about 0.15 to about 0.60 weight percent,
(vi) vanilla flavored ingredient: from about 0.70 to about 1.5 weight percent,
(vii) cotton candy flavored ingredient: from about 0.55 to about 1.10 weight percent,
(viii) glycerin: from about 5 to about 30 weight percent,
(ix) monoammonium glycyrrhizinate: from about 0.35 to about 0.65 weight percent,
(x) saccharin sodium: from about 0.05 to about 0.85 weight percent,
(xi) acesulfame potassium: from about 0.35 to about 0.85 weight percent, and
(xii) high fructose corn syrup: from about 14.5 to about 33.6 weight percent.

19. The liquid pharmaceutical composition of claim 1, wherein the one or more pharmaceutically active agents comprises derivatives of ritonavir.

20. The liquid pharmaceutical composition of claim 19 wherein components (i)-(xii) are present in the following weight percentages, based on the total weight of the pharmaceutical composition:
(i) citric acid: from about 0.10 to about 0.25 weight percent,
(ii) sodium citrate: not greater than about 0.25 weight percent,
(iii) sodium chloride: not greater than about 0.40 weight percent,
(iv) menthol flavored ingredient: from about 0.03 to about 0.25 weight percent,
(v) peppermint flavored ingredient: from about 0.15 to about 0.60 weight percent,
(vi) vanilla flavored ingredient: from about 0.70 to about 1.5 weight percent,
(vii) cotton candy flavored ingredient: from about 0.55 to about 1.10 weight percent,
(viii) glycerin: from about 5 to about 30 weight percent,
(ix) monoammonium glycyrrhizinate: from about 0.35 to about 0.65 weight percent,
(x) saccharin sodium: from about 0.05 to about 0.85 weight percent,
(xi) acesulfame potassium: from about 0.35 to about 0.85 weight percent, and
(xii) high fructose corn syrup: from about 14.5 to about 33.6 weight percent.

21. The liquid pharmaceutical composition of claim 1 further comprising a thickening agent.

22. The liquid pharmaceutical composition of claim 21, wherein the thickening agent is polyvinylpyrrolidone.

23. The liquid pharmaceutical composition of claim 1 further comprising a bioavailability enhancer.

24. The liquid pharmaceutical composition of claim 23, wherein the bioavailability enhancer is a castor oil derivative.

25. The liquid pharmaceutical composition of claim 1 wherein the one or more pharmaceutically active agents comprise
one or more derivatives of ritonavir and
one or more derivatives of lopinavir.

26. The liquid pharmaceutical composition of claim 25 wherein components (i)-(xii) are present in the following weight percentages, based on the total weight of the pharmaceutical composition:
(i) citric acid: from about 0.10 to about 0.25 weight percent,
(ii) sodium citrate: not greater than about 0.25 weight percent,
(iii) sodium chloride: not greater than about 0.40 weight percent,
(iv) menthol flavored ingredient: from about 0.03 to about 0.25 weight percent,
(v) peppermint flavored ingredient: from about 0.15 to about 0.60 weight percent,
(vi) vanilla flavored ingredient: from about 0.70 to about 1.5 weight percent,
(vii) cotton candy flavored ingredient: from about 0.55 to about 1.10 weight percent,
(viii) glycerin: from about 5 to about 30 weight percent,
(ix) monoammonium glycyrrhizinate: from about 0.35 to about 0.65 weight percent,
(x) saccharin sodium: from about 0.05 to about 0.85 weight percent,
(xi) acesulfame potassium: from about 0.35 to about 0.85 weight percent, and
(xii) high fructose corn syrup: from about 14.5 to about 33.6 weight percent.

27. The liquid pharmaceutical composition of claim 1, wherein the one or more pharmaceutically active agent is lopinavir.

28. The liquid pharmaceutical composition of claim 27, further comprising a solvent system comprising water, alkyl alcohols, and alkylene glycols, wherein said solvent system is present in an amount of between about 32% by weight and about 69% by weight based upon the total weight of the pharmaceutical composition.

29. The liquid pharmaceutical composition of claim 27 wherein components (i)-(xii) are present in the following weight percentages, based on the total weight of the pharmaceutical composition:
(i) citric acid: from about 0.10 to about 0.25 weight percent,
(ii) sodium citrate: not greater than about 0.25 weight percent,
(iii) sodium chloride: not greater than about 0.40 weight percent,
(iv) menthol flavored ingredient: from about 0.03 to about 0.25 weight percent,
(v) peppermint flavored ingredient: from about 0.15 to about 0.60 weight percent,
(vi) vanilla flavored ingredient: from about 0.70 to about 1.5 weight percent,
(vii) cotton candy flavored ingredient: from about 0.55 to about 1.10 weight percent,
(viii) glycerin: from about 5 to about 30 weight percent,
(ix) monoammonium glycyrrhizinate: from about 0.35 to about 0.65 weight percent,
(x) saccharin sodium: from about 0.05 to about 0.85 weight percent,
(xi) acesulfame potassium: from about 0.35 to about 0.85 weight percent, and
(xii) high fructose corn syrup: from about 14.5 to about 33.6 weight percent.

* * * * *

UNITED STATES PATENT AND TRADEMARK OFFICE
CERTIFICATE OF CORRECTION

| | | |
|---|---|---|
| PATENT NO. | : 8,501,219 B2 | Page 1 of 1 |
| APPLICATION NO. | : 12/687479 | |
| DATED | : August 6, 2013 | |
| INVENTOR(S) | : Alani et al. | |

It is certified that error appears in the above-identified patent and that said Letters Patent is hereby corrected as shown below:

In the Claims

Column 20, line 16, claim 11: "about 0.5" to read as --about 0.35--

Signed and Sealed this
Fourth Day of August, 2015

Michelle K. Lee
*Director of the United States Patent and Trademark Office*